US009880119B2

(12) United States Patent
Morosow et al.

(10) Patent No.: US 9,880,119 B2
(45) Date of Patent: Jan. 30, 2018

(54) APPARATUS FOR IDENTIFYING A VALUE OF A PROPERTY OF A FLUID WHICH IS TO BE MEASURED, METHOD FOR OPERATING AN APPARATUS FOR IDENTIFYING A VALUE OF A PROPERTY OF A FLUID WHICH IS TO BE MEASURED, AND METHOD FOR MANUFACTURING AN APPARATUS FOR IDENTIFYING A VALUE OF A PROPERTY OF A FLUID WHICH IS TO BE MEASURED

(71) Applicant: Robert Bosch GmbH, Stuttgart (DE)

(72) Inventors: Viktor Morosow, Reutlingen (DE); Dominik Geisler, Tuebingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 267 days.

(21) Appl. No.: 14/722,585

(22) Filed: May 27, 2015

(65) Prior Publication Data

US 2015/0346132 A1 Dec. 3, 2015

(30) Foreign Application Priority Data

May 27, 2014 (DE) ........................ 10 2014 210 122

(51) Int. Cl.
*G01N 19/00* (2006.01)
*G01N 27/22* (2006.01)

(52) U.S. Cl.
CPC ......... *G01N 27/226* (2013.01); *G01N 27/223* (2013.01)

(58) Field of Classification Search
CPC .. G01N 27/226; G01N 27/223; G01N 27/121; G01N 25/56; G01N 25/64;
(Continued)

(56) References Cited

U.S. PATENT DOCUMENTS 3,079,583 A * 2/1963 Beitscher ............ G01S 7/52006
331/59
4,212,194 A * 7/1980 Allen ....................... G01N 7/10
73/73

(Continued)

FOREIGN PATENT DOCUMENTS

DE 3781500 T2 4/1993
DE 19644290 A1 5/1998

(Continued)

OTHER PUBLICATIONS (English translation ) Franz, Bio-Chip with an electrode array on a substrate, Mar. 2006, Bosch GMBH Robert.*
Furry Elephant, Parallel Circuits, Jan. 2008, pp. 1-3.*

*Primary Examiner* — John Fitzgerald
*Assistant Examiner* — Truong D Phan
(74) *Attorney, Agent, or Firm* — Norton Rose Fulbright US LLP; Gerard Messina

(57) ABSTRACT

An apparatus is provided for identifying a property value of a fluid which is to be measured, a method for operating such an apparatus, and a method for manufacturing such an apparatus. The apparatus encompasses:
a measurement capacitor device bringable into contact with the fluid,
the measurement capacitor device having a first electrode, a second electrode, a first dielectric layer, and a second dielectric layer; a first dielectric constant of the first dielectric layer being dependent, in a context of contact with the fluid, on the property of the fluid to be measured;
a second dielectric constant of the second dielectric layer being substantially independent of the property of the fluid which is to be measured;
a compensation capacitor device that has the second dielectric layer, a third electrode, and a fourth electrode;

(Continued)

the compensation capacitor device connected in parallel, or connectable in parallel, with the measurement capacitor device.

9 Claims, 7 Drawing Sheets

(58) Field of Classification Search
CPC ........ G01N 25/60; G01N 25/68; G01N 25/62; G01N 31/222; G01N 2291/02845; G01N 29/036; G01N 2291/0256; G01N 27/185; G01N 30/66; G01N 27/18; G01N 27/4077; G01N 27/12; G01N 27/407; G01N 27/122; G01N 27/16; G01N 33/0016; G01N 33/246; G01N 27/225; G01N 27/048; G01N 33/0006; G01N 27/4175; G01N 33/007; G01F 23/268; G01R 27/2605; G06K 9/0002; G01D 5/24
USPC ....... 73/335.02, 335.04, 29.01, 29.02, 24.04, 73/25.04, 31.05, 23.21, 73, 1.06; 324/664, 690, 686, 689; 702/85; 318/643
See application file for complete search history.

(56) References Cited

U.S. PATENT DOCUMENTS

| | | | | |
|---|---|---|---|---|
| 5,269,175 | A * | 12/1993 | Chmiel | G01N 27/225 324/675 |
| 5,402,075 | A * | 3/1995 | Lu | G01R 1/07 324/664 |
| 6,411,107 | B1 * | 6/2002 | Ishikura | G01L 9/0072 324/658 |
| 6,577,140 | B1 * | 6/2003 | Wenman | G01N 33/2876 324/204 |
| 6,742,387 | B2 * | 6/2004 | Hamamoto | G01N 19/10 324/664 |
| 7,267,002 | B2 * | 9/2007 | Itakura | G01D 5/24 324/670 |
| 7,471,093 | B2 * | 12/2008 | Arisaka | G01N 27/225 324/664 |
| 2001/0003249 | A1 * | 6/2001 | Stormbom | G01N 27/223 73/1.06 |
| 2002/0140440 | A1 * | 10/2002 | Haase | H03K 17/955 324/678 |
| 2003/0222662 | A1 * | 12/2003 | Geisel | G01N 27/048 324/664 |
| 2004/0182153 | A1 * | 9/2004 | Hamamoto | G01N 27/225 73/335.04 |
| 2004/0194546 | A1 * | 10/2004 | Kanehori | G01N 27/225 73/335.04 |
| 2005/0068045 | A1 * | 3/2005 | Inaba | G01R 27/2605 324/678 |
| 2005/0174129 | A1 * | 8/2005 | Haider | G01R 27/2605 324/664 |
| 2011/0185810 | A1 * | 8/2011 | Humbert | G01N 27/223 73/335.04 |
| 2012/0234079 | A1 * | 9/2012 | Humbert | G01N 27/227 73/29.05 |
| 2013/0160518 | A1 * | 6/2013 | Leneel | G01N 27/228 73/1.06 |

FOREIGN PATENT DOCUMENTS

| | | |
|---|---|---|
| DE | 102 53 913 | 5/2003 |
| DE | 102004042729 A1 | 3/2006 |
| DE | 102006019534 A1 | 11/2007 |
| GB | 2136130 A | 9/1984 |
| WO | 85/04718 A1 | 10/1985 |
| WO | 87/06009 A1 | 10/1987 |

* cited by examiner

APPARATUS FOR IDENTIFYING A VALUE OF A PROPERTY OF A FLUID WHICH IS TO BE MEASURED, METHOD FOR OPERATING AN APPARATUS FOR IDENTIFYING A VALUE OF A PROPERTY OF A FLUID WHICH IS TO BE MEASURED, AND METHOD FOR MANUFACTURING AN APPARATUS FOR IDENTIFYING A VALUE OF A PROPERTY OF A FLUID WHICH IS TO BE MEASURED

FIELD OF THE INVENTION

The present invention relates to an apparatus for identifying a value of a property of a fluid which is to be measured, in particular to an at least partly micromechanical apparatus. It further relates to a method for operating an apparatus for identifying a value of a property of a fluid which is to be measured, in particular for operating an apparatus according to the present invention for identifying the value of the property of the fluid which is to be measured. Lastly, the present invention also relates to a method for manufacturing an apparatus for identifying a value of a property of a fluid which is to be measured, in particular to a method for manufacturing an apparatus according to the present invention for identifying the value of the property of the fluid which is to be measured.

A "fluid" is to be understood in particular as a gas or a liquid. The property of the fluid which is to be measured is in particular a physical and/or a chemical property. The property of the fluid which is to be measured can be, for example, a gas concentration, e.g. a moisture, a pH value, or the like. The "value" that is to be identified of the property that is to be measured is to be understood as a numerical value exhibited, at the time of measurement, by the property of the fluid which is to be measured, for example a pH of 7, a carbon dioxide concentration of 5%, etc.

BACKGROUND INFORMATION

A micromechanical sensor for identifying an atmospheric humidity value, also referred to as "atmospheric moisture," is described e.g. in DE 102 53 913 A1. A pair of oppositely located electrodes, which are comb-shaped and possess teeth, are embodied on a substrate. The teeth of the electrodes possess a generally uniform width and engage into one another. The teeth of one of the electrodes are separated from the teeth of the other electrodes by a generally uniform separating distance. The micromechanical sensor has a moisture-sensitive film whose capacitance changes with moisture; the moisture-sensitive film covers the electrodes and a region between the electrodes, and moisture is sensed on the basis of changes in capacitance between the electrodes in response to the changes in the humidity of the ambient air.

SUMMARY

The present invention discloses an apparatus, a method, and a manufacturing method.

The following is accordingly provided: an apparatus for identifying a value of a property of a fluid which is to be measured, having a measurement capacitor device that is bringable into contact with the fluid.

The measurement capacitor device has a first electrode, a second electrode, a first dielectric layer, and a second dielectric layer. The first electrode, the second electrode, the first dielectric layer, and the second dielectric layer are disposed in such a way that a first electrical capacitance of the measurement capacitor device is traceable at least in part to the first and the second electrode in conjunction with the first and with the second dielectric layer.

A first dielectric constant of the first dielectric layer is dependent, in a context of contact with the fluid, on the property of the fluid which is to be measured. A second dielectric constant of the second dielectric layer is substantially independent of the property of the fluid which is to be measured.

The apparatus furthermore has a compensation capacitor device that has the second dielectric layer, a third electrode, and a fourth electrode. The second dielectric layer, the third electrode, and the fourth electrode are disposed in such a way that a second electrical capacitance of the compensation capacitor device is traceable at least in part to the third and the fourth electrode in conjunction with the second dielectric layer.

The properties of the second dielectric layer in the measurement capacitor device and in the compensation capacitor device advantageously behave substantially similarly. In particular, material parameters, as well as geometric parameters that exhibit manufacturing-related variation and are to be identified for capacitance, of the second dielectric layer behave substantially similarly. Particularly preferably, a thickness of the second dielectric layer is substantially the same in the measurement capacitor device and in the compensation capacitor device.

The compensation capacitor device is connected in parallel, in particular is permanently connected in parallel, or is connectable in parallel, with the measurement capacitor device.

A "capacitor device", i.e. the measurement capacitor device and the compensation capacitor device, is intended in particular to encompass a capacitor of any design, for example a plate capacitor, wound capacitor, interdigital capacitor, spherical capacitor, etc. A capacitor device can furthermore encompass electrical terminals, connections, protective layers, insulating layers, a housing, seals, etc.

"Connected in parallel" is to be understood in particular to mean that the measurement capacitor device and the compensation capacitor device are interconnected in a circuit in such a way that the first electrical capacitance of the measurement capacitor device and the second electrical capacitance of the compensation capacitor device can be represented in an equivalent circuit diagram for the circuit by a first and a second electrical capacitance connected in parallel in a parallel connection. According to a refinement, the parallel connection is permanent.

"Connectable in parallel" is to be understood to mean that the parallel connection is not permanent but can be created, for example by way of a switch or an integrated circuit. Advantageous, connection in parallel is accomplished by way of an electronic circuit device, in particular an integrated electronic circuit, in particular automatically as a consequence of a program sequence. "Connectable in parallel" is furthermore also to be understood in particular as a reversible connectability in parallel. In other words, the connectability in parallel can also be associated with the fact that the compensation capacitor is uncouplable from the measurement capacitor device.

Also proposed is a method for operating an apparatus for identifying a value of a property of a fluid which is to be measured, in particular an apparatus according to the present invention as described above and hereinafter, having the steps of: bringing a measurement capacitor device into contact with a reference fluid, the reference fluid having a predetermined reference value of the property that is to be identified; a first electrical capacitance of the measurement capacitor device being made up of a first capacitance component and of a second capacitance component; the first capacitance component being dependent, in a context of contact with the reference fluid, on the property that is to be measured; and the second capacitance component being substantially independent of the property that is to be measured; measuring, while at least the measurement capacitor device is brought into contact with the reference fluid, a first instantaneous capacitance value of a total electrical capacitance of a parallel electrical circuit of the measurement capacitor device with a compensation capacitor device; the compensation capacitor device having a second electrical capacitance; the second electrical capacitance being substantially independent of the property that is to be measured; and the second electrical capacitance having a substantially known correlation with the second electrical capacitance component of the measurement capacitor device; and identifying, based on the measured first instantaneous capacitance value and on the predetermined first reference value of the property of the reference fluid which is to be measured, a sensitivity of the apparatus with respect to the property that is to be measured.

Also provided is a method for manufacturing an apparatus for identifying a value of a property of a fluid which is to be measured, in particular for manufacturing an apparatus according to the present invention as described above and hereinafter, having the steps of: embodying a measurement capacitor device that is bringable into contact with the fluid; the embodying of the measurement capacitor device being accomplished in such a way that the measurement capacitor device is embodied with a first electrode and a second electrode and with a first dielectric layer and a second dielectric layer; a first dielectric constant of the first dielectric layer being dependent, in a context of contact with the fluid, on the property of the fluid which is to be measured; and a second dielectric constant of the second dielectric layer being substantially independent of the property of the fluid which is to be measured; the measurement capacitor device furthermore being embodied in such a way that the measurement capacitor device has a first electrical capacitance that is traceable at least in part to the first and the second electrode in conjunction with the first dielectric layer and the second dielectric layer; embodying a compensation capacitor device that has the second dielectric layer, a third electrode, and a fourth electrode; the compensation capacitor device furthermore being embodied in such a way that the compensation capacitor device has a second electrical capacitance that is traceable at least in part to the third and the fourth electrode in combination with the second dielectric layer.

The fundamental realization of the present invention is that in apparatuses, in particular at a wafer level, for measuring physical properties of substances, manufacturing-related deviations from target values, for example target values for layer thicknesses of functional layers, can result in errors in measurement results when identification of the measurement results is based on the target values. The measurement methods described in this application are capacitive measurement methods, so that the functional layers are dielectric layers, i.e. layers whose dielectric constants are measured in a context of utilization as intended of the apparatus according to the present invention, whether individually or in an assemblage of capacitive elements, for example a series circuit or parallel circuit, e.g. as defined by an equivalent circuit diagram. The term "dielectric constant" is historical in origin and is not intended to mean that the parameter referred to as a "dielectric constant" is constant; in particular, the measurement methods described are based on a change in the variable dielectric constant of a functional layer in a context of contact with a fluid.

For example, the dielectric constant of a polyimide layer can change under the influence of a humidity of a fluid, for example an atmospheric humidity. "Atmospheric humidity" is to be understood in particular as a concentration of water vapor in air. It is also possible to embody at least one functional dielectric layer from one or more materials whose dielectric constant changes, in a context of contact with a liquid, based on the pH of the liquid. It is moreover also possible to embody at least one functional dielectric layer from one or more materials whose dielectric constant changes, in a context of contact with a fluid, based on a carbon dioxide concentration in the fluid.

In the manufacture of a sensor, equalization is an essential step. Here firstly a determination is made as to how the measurement result of a sensor, i.e. the signal at the end of a signal chain (e.g. capacitance/voltage converter and voltage/numerical value converter) changes as a function of the applied stimulus (e.g. humidity) or the applied stimuli (e g humidity and temperature). It is then possible to identify, in one or more iterations, parameters that enable back-calculation of the stimulus from the end result of the signal chain. This can be done both by (preferably iterative) manipulation of the signal chain and by way of a second signal chain or processing chain downstream from the first signal chain. Application of the stimuli is cost-relevant, and it is desirable to minimize the number of defined equalization points that must be traveled to. If only one known stimulus is applied, this is called "single-point equalization."

The underlying idea of the invention is thus to take the above-described realization into account by the fact that an apparatus for identifying a value of a property of a fluid which is to be measured is embodied with a measurement capacitor device that serves principally to identify the value, and is embodied with a compensation capacitor device that is suitable for decreasing the influence of manufacturing-related deviations from the target values on the identification of the value, in particular on the preceding identification of the sensitivity of the apparatus with respect to a change in the property that is to be measured. Decreasing this influence allows the errors in identification of the value to be reduced so that even with single-point equalization for calibration of the apparatus, the errors in identification of the value remain within comparatively narrow error thresholds, for example within +/−5%, preferably within +/−3% or even less. The error thresholds can also be located asymmetrically around the exact value, for example −1% to +3%.

In a single-point equalization, for an individual component (here one of the apparatuses according to the present invention) a single measurement point is generated in controlled circumstances, in this case by measuring a reference value of the property that is to be identified. Single-point equalization is less technically complex than multi-point equalization. Each individual component is subject to manufacturing-related fluctuations, i.e. deviations from target values. Based on the individual measurement point, the individual component is calibrated. In the present case, as part of a calibration, a sensitivity of the individual apparatus according to the present invention with respect to a change in the property of the fluid which is to be identified is also identified.

Once the sensitivity is known, an instantaneous value of the property of the fluid which is to be identified can be identified from an instantaneous measurement point on the fluid by comparison with the known measurement point that was generated under the controlled conditions. For example, if it is known that an electrical capacitance of an apparatus has a value of one unit as offset when the atmospheric humidity is equal to 10% as a reference value; and furthermore if the sensitivity of the apparatus is known, i.e. the extent to which the electrical capacitance of the apparatus changes in the context of a given change in atmospheric humidity, it is then possible to identify from the instantaneous measurement point, which indicates e.g. an instantaneous electrical capacitance of the apparatus of three units, the instantaneous value for the atmospheric humidity.

In a multi-point measurement two or more measurement points, between which, for example, a linear correlation is assumed, are identified for an individual component. The result is that the calibration accuracy can be improved but the calibration outlay increases.

A simple single-point equalization based on an exemplifying apparatus 1 for capacitive measurement of an atmospheric humidity is explained with reference to FIG. 9. Disposed between three capacitor plates 2 is a functional layer 3 made of a polyimide, the dielectric constant of which depends, in material-related fashion, on the atmospheric humidity H of the ambient air. Capacitor plates 2 and functional layer 3 are disposed on a substrate 5, and an insulating layer 4 insulates substrate 5 from capacitor plates 2. A voltage can be applied via two contact devices 6 in order to measure the electrical capacitance of apparatus 1.

The formula for the electrical capacitance C(H) of this assemblage as a function of atmospheric humidity H is $$C(H) = \varepsilon_0 \varepsilon_{pol}(H) \frac{A}{d}$$

where $\varepsilon_0$ is the electric field constant, $\varepsilon_{pol}$ the atmospheric humidity-dependent dielectric constant of the polyimide used, A the effective area of the plate capacitor, and d the effective distance between the two capacitor plates of the plate capacitor which extends perpendicular to the effective area A. Both the effective area A and the distance d can be subject to manufacturing-related deviations from a respective target value. The deviations of the area A from the target value are not considered in this application; they are often relatively small in relation to the area A itself.

The sensitivity to atmospheric humidity is the total derivative of the electrical capacitance over atmospheric humidity H:

$$S = \frac{\delta C(H)}{\delta H} = \varepsilon_0 \frac{A}{d} \frac{\delta \varepsilon_{pol}(H)}{\delta H}.$$

When the above capacitance C(H0) of the atmospheric humidity H is measured at a predetermined reference value H0, the term $$\varepsilon_0 \frac{A}{d} = \frac{C(H_0)}{\varepsilon_{pol}(H_0)}$$

can be measured, where $\varepsilon_{pol}(H0)$ is previously known from tables and/or measurement series. Using the value for $$\frac{\delta \varepsilon_{pol}(H)}{\delta H}$$

that is likewise previously known from tables and/or measurement series, the sensitivity S can thus be calculated particularly accurately as $$S = \frac{C(H_0)}{\varepsilon_{pol}(H_0)} \frac{\delta \varepsilon_{pol}(H)}{\delta H}.$$

If a capacitance C(H1) is then measured at an atmospheric humidity value H1 in the actual measurement, this atmospheric humidity value H1 can be identified most easily as $$H_1 = H_0 + S[C(H_1) - C(H_0)],$$

wherein $S[C(H_1)-C(H_0)]$ represents S as a function of the differential between the capacitance values at $H_1$ and at $H_0$ since S is a function of C(H)/H.

i.e. the atmospheric humidity value H1 is the sum of the reference value H0 of the atmospheric humidity as offset, plus the product of the sensitivity S times the difference between the capacitance in a context of contact with air having the atmospheric humidity value H1 and the capacitance in a context of contact with air having the atmospheric humidity value H0. It would be even more accurate to speak in each case not of a "capacitance" but rather of a respective instantaneous capacitance value of the electrical capacitance.

Electrodes of such apparatuses for capacitive identification of values for properties of a substance which are to be measured can be equipped with protective layers, for example oxygen-impermeable protective layers to prevent oxidation of the electrodes or moisture-impermeable protective layers to prevent corrosion of the electrodes and thus to extend the service life of the apparatus and stabilize the apparatus' behavior over the service life. This can yield a capacitive series circuit whose total electrical capacitance contains as unknowns both the layer thickness of the protective layer and the layer thickness of the functional layer used in the apparatus, the dielectric constant of which can change in a context of contact with the fluid.

According to the inventive idea of the present patent application, a single-point equalization, i.e. a calibration based on a single-point measurement, can also be carried out for an apparatus for identifying a value of a property of a fluid which is to be measured, in which context measurement errors that are based on manufacturing-related deviations from target values are minimized. The target value for one of the dielectric layers of the apparatus whose dielectric constant does not depend on the value of the property of the fluid which is to be measured, for example for a protective layer, can be used for the calculations. According to the present invention, the errors that can occur in the context of identification of the sensitivity of the apparatus as a result of manufacturing-related deviations in the protective layer of this dielectric layer can be decreased by way of the compensation capacitor device.

In the above-described methods for operating the apparatus for identifying the value of the property of the fluid which is to be measured, some steps can serve to calibrate the respective individual apparatus. These are in particular steps that result in identification of the sensitivity of the apparatus and in identification of an offset. The sensitivity and the offset are, for example, described above with reference to FIG. 9. Because of the outlay associated with them, the calibration steps can advantageously be carried out only once, while the further steps, i.e. the actual identification of the value of the property of the fluid which is to be measured, can be carried out as often as desired later in time than the calibration steps.

According to a preferred refinement of the apparatus according to the present invention, the first dielectric layer and the second dielectric layer are embodied between the first electrode and the second electrode. According to a further preferred refinement, the second dielectric layer is embodied between the third electrode and the fourth electrode. Advantageously, only the second dielectric layer is embodied between the third electrode and the fourth electrode. The measurement accuracy of the apparatus can thereby be further improved.

According to a further preferred refinement the apparatus has a measurement device with which a first instantaneous capacitance value of a total electrical capacitance of a parallel electrical circuit of the measurement capacitor device with the compensation capacitor device is measurable. According to a further preferred refinement, the apparatus has an identification device with which, based on the measured first instantaneous capacitance value, a sensitivity of the apparatus with respect to the property that is to be measured is identifiable.

According to a further preferred refinement the apparatus has a computation device with which, based on the identified sensitivity of the apparatus and based on a measured second instantaneous capacitance value of the first electrical capacitance of the measurement capacitor device, and/or based on a measured third instantaneous capacitance value of the total electrical capacitance of the parallel circuit of the measurement capacitor device with the compensation capacitor device, the value that is to be identified of the property of the fluid which is to be measured is identifiable. The apparatus can be of particularly compact configuration as a result. In addition, production steps can be combined in particular at a wafer level, so that the technical outlay for manufacturing the apparatus is decreased.

The identification device and/or the computation device can be embodied, for example, as a computer of an equalization system.

According to a further preferred refinement the first dielectric layer encompasses a polyimide or is made of a polyimide. Polyimides have dielectric constants that change almost linearly with an applied relative atmospheric humidity, i.e. one that is brought into contact. Polyimides are thus particularly suitable for an apparatus for measuring an atmospheric humidity, in particular a relative atmospheric humidity, in accordance with the present invention. A drift in the properties of polyimides is also comparatively low. Polyimides can be integrated in many ways, and depending on size can result, over an exemplifying measurement range between 0% and 100% relative atmospheric humidity, for example in capacitance changes in the range from a hundred to a thousand femtofarad, or even several tens of thousand femtofarad depending on the dimensions of the polyimides. As will also be described below, capacitance changes of this kind can easily be evaluated using integrated circuits in order to identify the atmospheric humidity.

According to a further preferred refinement the measurement capacitor device is embodied as a plate capacitor or as an interdigital capacitor. If the measurement capacitor is embodied as a plate capacitor, one or more electrodes of the measurement capacitor device can be made of a porous or moisture-permeable material so that the fluid, or its moisture, can penetrate through said electrode. According to a further preferred refinement the compensation capacitor device is embodied as a plate capacitor or as an interdigital capacitor. Capacitor shapes of these kinds for the capacitor devices are particularly compact and easy to manufacture.

According to a further preferred refinement the fluid is a gas or a gas mixture, and the property of the gas or gas mixture which is to be identified is a concentration of a predetermined substance in the gas or gas mixture, for example a carbon dioxide content in air. According to a particularly preferred refinement the fluid is a gas or gas mixture, for example air, and the property to be identified is a concentration of water vapor in the gas or gas mixture, the first dielectric constant of the first dielectric layer changing substantially as a function of the concentration of water vapor in the gas or gas mixture.

According to a further preferred refinement the fluid is a liquid, and the property of the liquid which is to be identified is a pH of the liquid.

According to a further preferred refinement the apparatus has a controllable circuit device with which the compensation capacitor device is electrically connectable in parallel with the measurement capacitor device and/or electrically decouplable from the measurement capacitor device. At least the measurement capacitor device and the compensation capacitor device are embodied on one and the same substrate. According to a further preferred refinement the controllable circuit device is embodied as an application-specific integrated circuit disposed on the substrate. The apparatus can thus be produced in particularly compact fashion and at a wafer level, with particularly little technical outlay. What can be achieved by decoupling the compensation capacitor device is that it is not also constantly stressed in the context of actual measurement. This can be advantageous if, for example, it is to be expected that the compensation capacitor device will age differently, for example faster, than the measurement capacitor device, or if no information exists regarding long-term behavior.

According to a further preferred refinement the circuit device is embodied as an application-specific integrated circuit that is separate from the substrate and electrically connected to the measurement capacitor device and to the compensation capacitor device.

According to a preferred refinement the method according to the present invention for operating an apparatus for identifying a value of a property of a fluid which is to be measured has the further steps of: measuring a fourth instantaneous capacitance value of the first electrical capacitance of the measurement capacitor device in a context of contact between the measurement capacitor device and the reference fluid, the reference fluid having a predetermined reference value of the property of the reference fluid which is to be measured; bringing the measurement capacitor device into contact with the fluid having the property that is to be measured; measuring a second instantaneous capacitance value of the measurement capacitor device in a context of contact between the measurement capacitor device and the fluid having the property that is to be measured; calculating the value that is to be identified of the property of the fluid which is to be measured, based on the measured second instantaneous capacitance value; furthermore based on identified sensitivity of the apparatus with respect to the property that is to be measured; and based on the measured fourth instantaneous capacitance value. The measurement accuracy of the method according to the present invention can thereby be further improved.

According to a further preferred refinement the method encompasses the step of: ascertaining a difference value between the measured first and the measured fourth instantaneous capacitance value; calculation of the value that is to be identified of the property of the fluid which is to be identified being carried out based on the ascertained difference value between the measured first and the measured fourth instantaneous capacitance value.

According to a further preferred refinement the method encompasses the steps of: bringing the measurement capacitor device into contact with the fluid having the property that is to be measured; measuring a third instantaneous capacitance value of the total electrical capacitance of the measurement capacitor device with the compensation capacitor device in a context of contact between the measurement capacitor device and the fluid; calculating the value that is to be identified of the property of the fluid which is to be measured, based on the measured third instantaneous capacitance value; and further based on the identified sensitivity of the apparatus with respect to the property that is to be measured.

According to a preferred refinement of the method according to the present invention for manufacturing an apparatus, the first dielectric layer and the second dielectric layer are embodied between the first electrode and the second electrode. According to a further preferred refinement the second dielectric layer is embodied between the third electrode and the fourth electrode.

According to a further preferred refinement the second dielectric layer is embodied in the same production step between the first electrode and the second electrode, and between the third electrode and the fourth electrode. Manufacturing-related deviations in the properties, in particular dimensions, among them layer thicknesses, of the second dielectric layer thus act in the same manner both on the measurement capacitor device and on the compensation capacitor device, and can thus be compensated for. In other words, the influence of these deviations on the identification of the sensitivity of the apparatus with respect to changes in the property of the fluid which is to be measured can be decreased.

When elements are referred to in this description and in the Claims as "first," "second," "third," "n-th," etc., it is to be understood that this involves not a numerical enumeration, but merely different designations. It is thus entirely possible for an element referred to as "second" to be contained in a specific embodiment with no need for an element referred to as "first" also to be necessarily contained in that embodiment.

BRIEF DESCRIPTION OF THE DRAWINGS

In all the Figures, identical or functionally identical elements and apparatuses are labeled, unless otherwise indicated, with the same reference characters.

DETAILED DESCRIPTION

Figure 1:
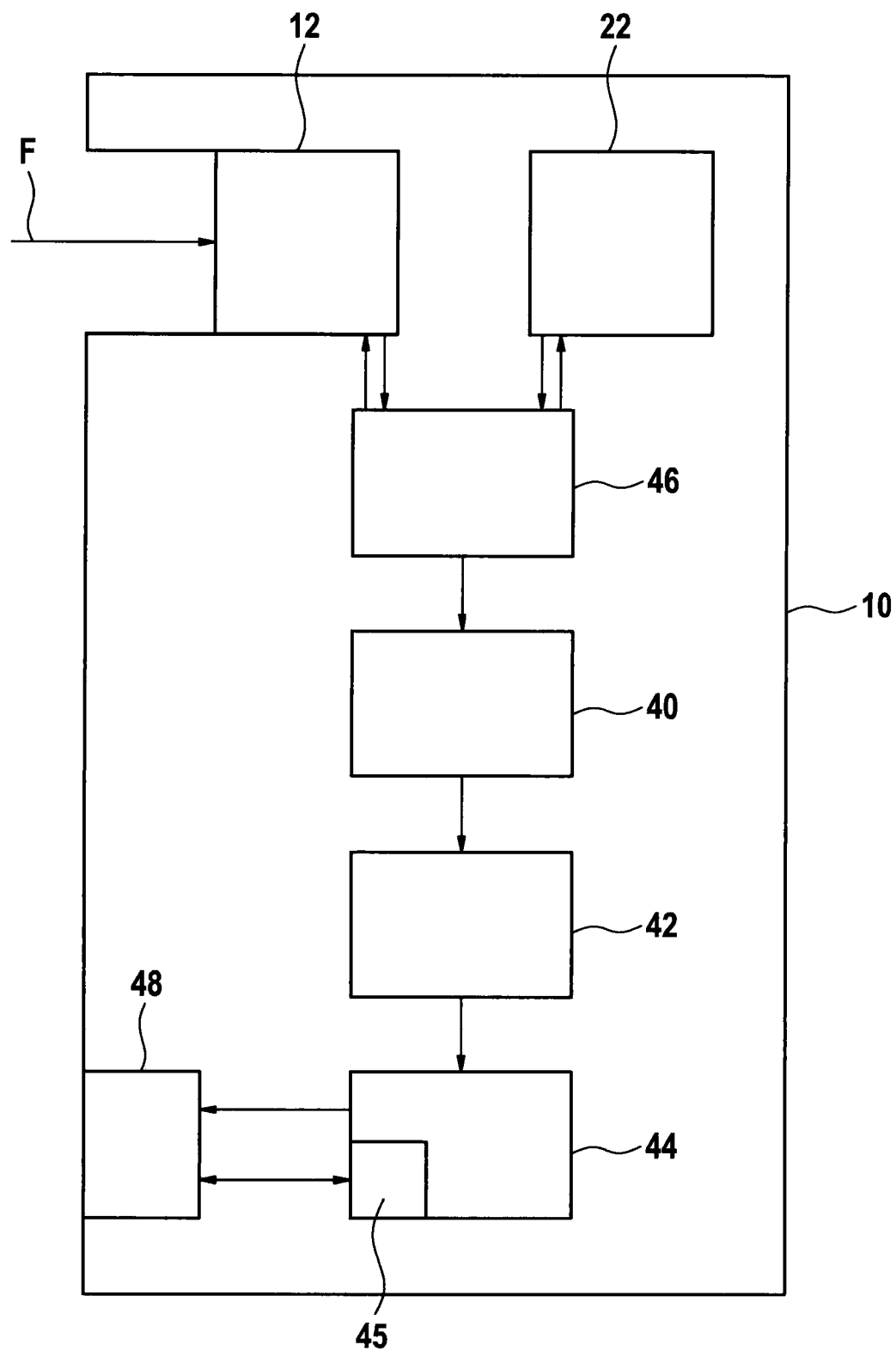
FIG. 1 is a schematic block diagram of an apparatus for identifying a value of a property of a fluid which is to be measured, according to a first embodiment of the present invention.

FIG. 1 is a schematic block diagram of an apparatus 10 for identifying a value of a property of a fluid F which is to be measured, according to a first embodiment of the present invention. The reader is also referred to the subsequent FIGS. 2 to 5 for details.

According to the first embodiment, apparatus 10 has a measurement capacitor device 12 that is bringable into contact with fluid F. Measurement capacitor device 12 can for this purpose be disposed on an outer surface of apparatus 10. In particular, apparatus 10 according to the first embodiment is an apparatus for measuring an atmospheric humidity, i.e. a concentration of water in air constituting fluid F.

Figure 2:
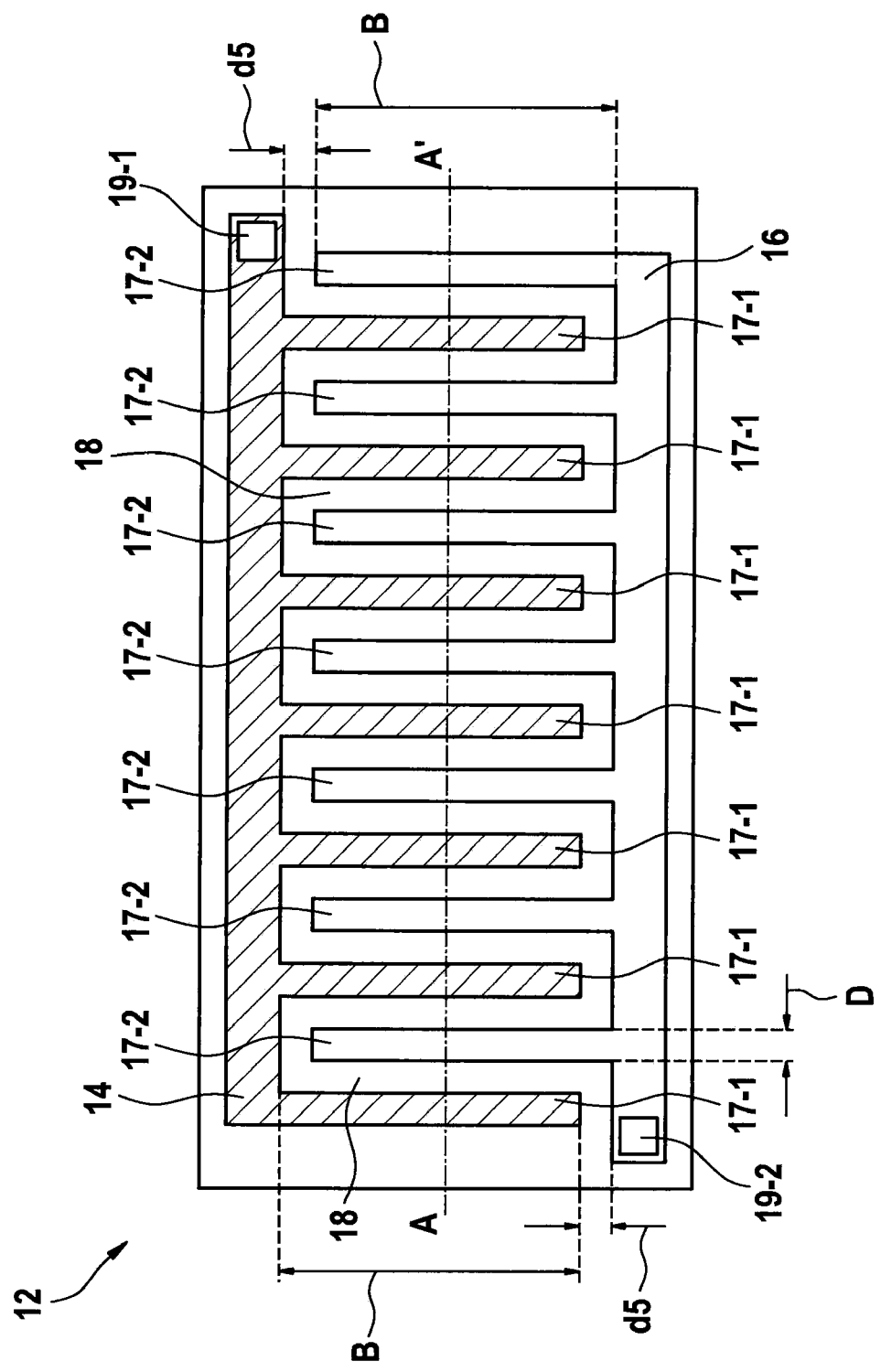
FIG. 2 is a schematic cross-sectional view of a measurement capacitor device of the apparatus according to the first embodiment of the present invention.

FIG. 2 is a schematic cross-sectional view of a measurement capacitor device 12 of apparatus according to the first embodiment. Measurement capacitor device 12 is embodied as an interdigital capacitor (see also FIGS. 2 and 3). An interdigital capacitor of this kind has comb-shaped electrodes disposed so as to engage "interdigitally" (like meshing fingers) into one another. The individual teeth of the comb shape of the electrodes will hereinafter be referred to as "electrode fingers."

Measurement capacitor device 12 has a first electrode 14 having a first plurality of electrically connected first electrode fingers 17-1 and a second electrode 16 having a second plurality of electrically connected electrode fingers 17-2. With the exception of electrode fingers 17-1, 17-2 embodied at an edge of measurement capacitor device 12, a respective first electrode finger 17-1 engages into a gap between two of the second electrode fingers 17-2, and a respective second electrode finger 17-2 engages into a gap between two of the first electrode fingers 17-1. First and second electrode 14, 16 are made of a conductive material, in particular of polysilicon or of a metal, preferably aluminum, copper, titanium, or tungsten. One or more of the electrodes can be made of a porous metal in order to enable better access by fluid F into or onto measurement capacitor device 12.

Electrode fingers 17-1, 17-2 extend, in cross section, perpendicular to a common imaginary axis A-A'. Each of the first and second electrode fingers 17-1, 17-2 is embodied substantially as a plate in a respective plane perpendicular to axis A-A'. Electrode fingers 17-1, 17-2 each have a width B perpendicular to axis A-A' and a thickness D parallel to axis A-A'. It is to be understood here that shapes can be indicated only substantially due to the manufacturing methods used. Instead of an ideal plate having rectangular cross sections, for example, electrode fingers 17-1, 17-2 can exhibit one or more trapezoidal, triangular, and/or pentagonal cross sections, etc.

First and second electrode 14, 16 and the associated first and second electrode fingers 17-1, 17-2 are made of an electrically conductive material, in particular of a metal. First electrode 14 is electrically contactable via a first electrical contact device 19-1, for example a bonding pad. Second electrode 16 is electrically contactable via a second electrical contact device 19-2, for example a bonding pad. A first dielectric layer 18, which will be further explained below, is embodied between electrode fingers 17-1, 17-2 of the first and second electrodes 14, 16.

Figure 3:
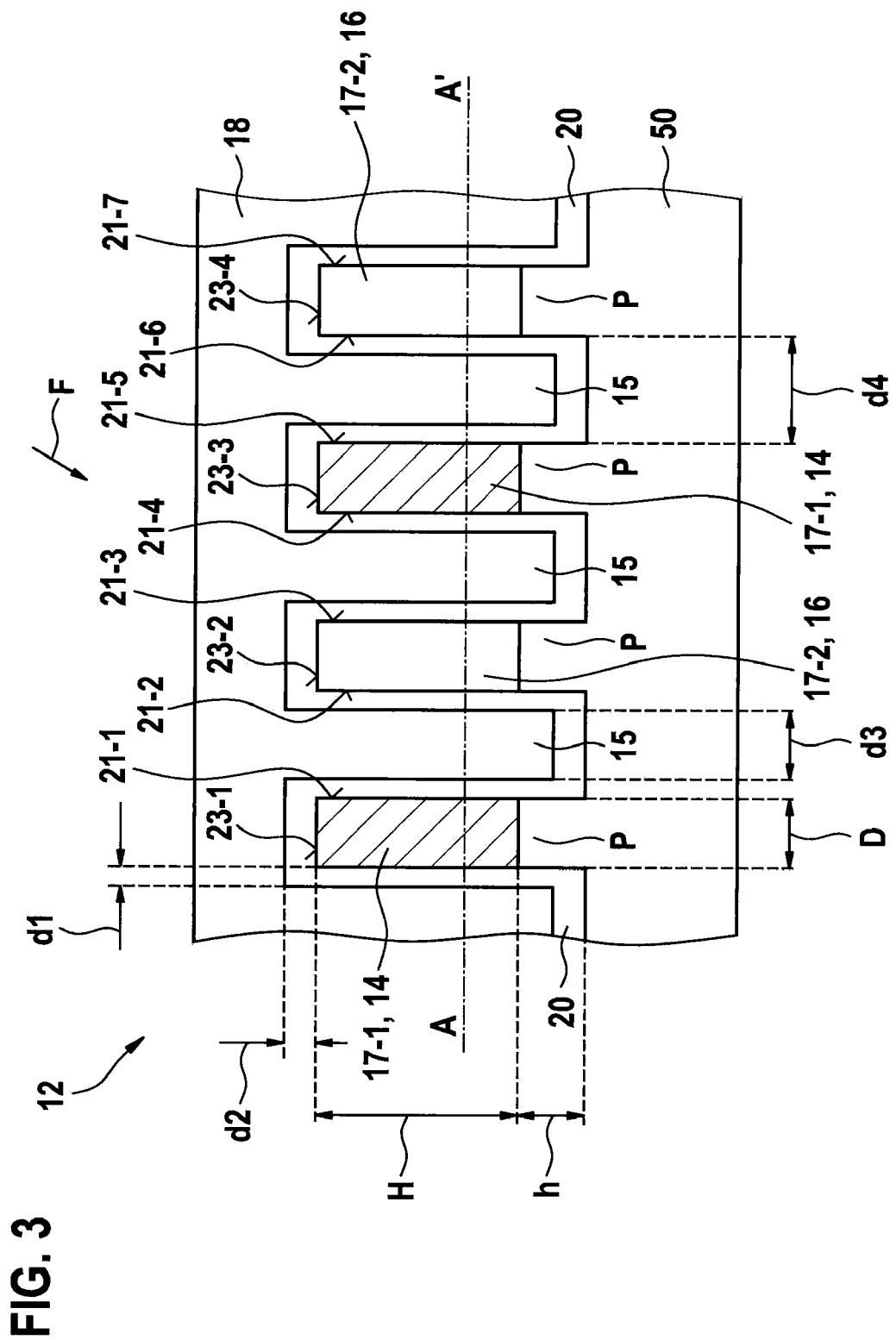
FIG. 3 is a schematic longitudinal sectional view of the measurement capacitor device of the apparatus according to the first embodiment of the present invention.

FIG. 3 is a schematic longitudinal sectional view of the apparatus according to the first embodiment, which view encompasses the axis A-A' and extends perpendicularly to the cross section shown in FIG. 2. As depicted in FIG. 3, electrode fingers 17-1, 17-2 according to the first embodiment are each embodied with a height H perpendicular to axis A-A'. First and second electrode 14, 16 are embodied on a common substrate 50. The substrate is preferably a non-conductive silicon substrate, for example made of silicon oxide; other materials are also conceivable. First and second electrode 14, 16 are embodied in the same plane, insulated from one another.

The substrate is embodied, for example by etching before or after application of electrode fingers 17-1, 17-2 onto substrate 50, with pedestals P spaced apart from one another. Pedestals P have substantially a pedestal height h with respect to substrate 50, as well as likewise a thickness D and width B. Each of the first and second electrode fingers 17-1, 17-2 is embodied, with a height H, on a respective pedestal P of substrate 50. An insulating layer, for example an oxide layer made e.g. of silicon oxide, can be embodied between pedestals P and electrode fingers 17-1, 17-2. Alternatively, electrode fingers 17-1, 17-2 can also be embodied directly on substrate 50. Pedestals P can contribute to preventing undesired electrical connections between first and second electrode 14, 16 when electrode fingers 17-1, 17-2 are embodied.

Electrode fingers 17-1, 17-2 are coated with a second dielectric layer 20 as a protective layer, which can serve in particular to improve the reliability and/or to extend the service life of measurement capacitor device 12. According to the first embodiment, second dielectric layer 20 is made of silicon nitride. Silicon nitride layer 20 can be, for example, vacuum-deposited onto substrate 50 having electrode fingers 17-1, 17-2 disposed thereon. Alternatively, the second dielectric layer can also be made, for example, of gold, of another silicon oxide, or of another gas-tight, non-oxidizing material.

Silicon nitride layer 20 is embodied with a first layer thickness d1 on surfaces 21-1 to 21-7 of electrode fingers 17-1, 17-2 which face toward one or more other electrode fingers 17-1, 17-2. Silicon nitride layer 20 is embodied with a second layer thickness d2 on surfaces 23-1 to 23-4 facing away from substrate 50, first layer thickness d1 being less than second layer thickness d2.

Between electrode fingers 17-1, 17-2 and a side of first and second electrodes 14, 16 which faces away from substrate 50, first dielectric layer 18 is embodied as a polyimide layer. In particular, gaps 15 between electrode fingers 17-1, 17-2 are filled as completely as possible with second dielectric layer 20. A gap width d4 of gaps 15 between electrode fingers 17-1, 17-2 is preferably between 200 nanometers and 2000 nanometers, in particular between 500 nanometers and 1500 nanometers in width. The third layer thickness d3 of first dielectric layer 18 between electrode fingers 17-1, 17-2 can be, in particular, between 100 nanometers and 500 nanometers thinner than gap width d4.

Advantageously, gap width d4 is embodied to be substantially consistent for all electrode fingers 17-1, 17-2. A space d5 between tips of electrode fingers 17-1, 17-2 and a main body of first and second electrodes 14, 16 from which electrode fingers 17-1, 17-2 proceed (see FIG. 2) can advantageously be between half and twice the gap width d4. In particular, distance d5 can also be equal to the gap width d4.

A first electrical capacitance C1 of measurement capacitor device 12 accordingly has a first and a second capacitance component Cm, Cp. The first capacitance component Cm is traceable to first and second electrode 14, 16 in conjunction with first dielectric layer 18, i.e. the polyimide layer. The polyimide layer is constituted, i.e. the polyimide or polyimides of the second dielectric layer is or are selected, in such a way that a first dielectric constant of first dielectric layer 18 is variable as a function of an atmospheric humidity of the ambient air constituting fluid F, i.e. it changes as a function of atmospheric humidity. The first capacitance component Cm is thus also dependent on atmospheric humidity. On that basis a capacitive measurement for identifying the atmospheric humidity, constituting a property of the air which is to be identified, can be carried out.

The second capacitance component Cp of the first electrical capacitance C1 of measurement capacitor device 12 is traceable to first and second electrode 14, 16 in conjunction with second dielectric layer 20, i.e. the silicon nitride layer. The second dielectric layer, embodied as a silicon nitride layer, has a second dielectric constant of second dielectric layer 20 which is substantially independent of atmospheric humidity.

The second capacitance component Cp is thus also substantially independent of atmospheric humidity, with the result that the sensitivity of the measurement capacitor device to changes in atmospheric humidity can decrease. In terms of electrical engineering, the first and the second capacitance component Cm, Cp are connected in series (see FIG. 5), thus yielding the first electrical capacitance C1.

The first layer thickness d1 of second dielectric layer 20 is subject to fluctuations depending on the manufacturing method selected, for example vacuum deposition. A target value for the first layer thickness d1 can be, for example, between 30 and 250 nanometers, preferably between 40 and 150 nanometers, in particular 60 to 100 nanometers. A different layer thickness on the end sides and flank sides of electrode fingers 17-1, 17-2 is possible for manufacturing reasons. For example, the first layer thickness d1 can be 40% less than the second layer thickness d2. Fluctuations of, for example, plus or minus 10% can occur in this context for manufacturing reasons. Because first dielectric layer 18 is filled into gaps 15, having the gap width d4, between electrode fingers 17-1, 17-2 after the formation of second dielectric layer 20 on electrode fingers 17-1, 17-2, a third layer thickness d3 of first dielectric layer 18 between electrode fingers 17-1, 17-2 is also subject to manufactured-related fluctuations.

A sensitivity of apparatus 10 with respect to a change in atmospheric humidity is traceable to a change in the first capacitance component Cm. The greater the change in the first capacitance component Cm (especially in terms of a percentage of the first capacitance component Cm) between a contact with air having approximately 0% relative humidity and a contact with air having approximately 100% relative humidity, the greater the sensitivity of apparatus 10 with respect to a change in atmospheric humidity.

Advantageously, a single-point equalization is used in identifying the sensitivity. Here apparatus 10 is brought into contact with a reference fluid having a predetermined reference value of the property of the fluid which is to be identified, in the presently described example with air having a relative humidity of 50%. Based thereon, the sensitivity of apparatus 10 is identified as described in further detail below, the target values being assumed for the first and third layer thicknesses d1, d3. A target value for the third layer thickness d3 can be, for example, between 100 and 2000 nanometers, advantageously between 200 and 1500 nanometers, in particular between 300 and 1300 nanometers, and particularly preferably can be 300 nanometers. Because the first and third layer thicknesses d1, d3 deviate from the target values for manufacturing reasons, the sensitivity of apparatus 10 is thus identified with a certain error. The dependence of the identification of the sensitivity on the manufacturing-related deviations of the first and third layer thicknesses d1, d3 is decreased by way of compensation capacitor apparatus 22, so that even with a single-point equalization, the resulting error in the identification of the sensitivity remains relatively small.

It is therefore advantageous if the fluctuations in particular of the first and third layer thicknesses d1, d3 result in the smallest possible error in the identification of the atmospheric humidity value based on measured electrical capacitances, which encompass the first capacitance component Cm. This is achieved by way of a compensation capacitor device 22, as described in further detail below.

Referring again to FIG. 1, apparatus 10 furthermore has a compensation capacitor device 22 that, according to the first embodiment, is embodied as a plate capacitor.

Figure 4:
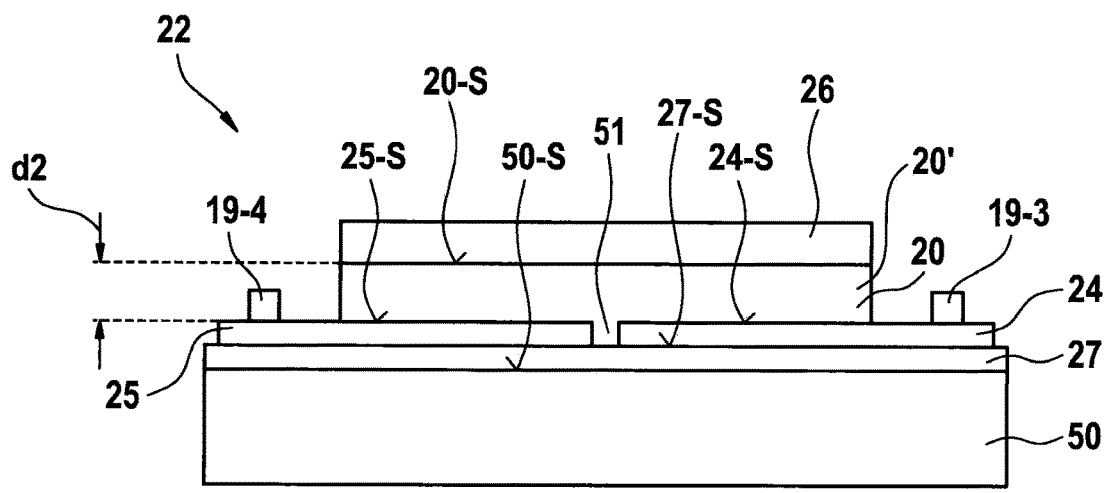
FIG. 4 is a schematic cross-sectional view of a compensation capacitor device of the apparatus according to the first embodiment of the present invention.

FIG. 4 is a schematic cross-sectional view of a compensation capacitor device 22 of apparatus 10 according to the first embodiment. According to the first embodiment, compensation capacitor device 22 is embodied as a plate capacitor on a surface 50-S of substrate 50 on which measurement capacitor device 12 is also embodied.

An electrically insulating layer, in particular an oxide layer 27, is embodied on a surface 50-S of substrate 50. A third electrode 24 and a fifth electrode 25, spaced apart from each other by a gap 51, are embodied on, in particular at, a surface 27-S of oxide layer 27 which faces away from the substrate. Third and fifth electrode 24, 25 are made of an electrically conductive material, in particular of polysilicon or of a metal, preferably aluminum, copper, titanium, or tungsten. Third and fifth electrode 24, 25 of compensation capacitor device 22 can advantageously be manufactured in the same production step and with the same method as first and second electrode 14, 16 of measurement capacitor device 12.

Second dielectric layer 20 is embodied on, in particular at, a surface 24-S of third electrode 24 which faces away from oxide layer 27. A segment 20' of second dielectric layer 20 which is part of compensation capacitor device 22 can be separate and spaced apart from a segment of second dielectric layer 20 which is part of measurement capacitor device 12. Second dielectric layer 20 can be patterned for this purpose, for example by etching.

Alternatively, second dielectric layer 20 can also be embodied continuously, i.e. integrally, so that segment 20' of second dielectric layer 20 which is part of compensation capacitor device 22, and that segment of second dielectric layer 20 which is part of measurement capacitor device 12, are connected to one another within the second dielectric layer.

According to the first embodiment, the entire second dielectric layer 20 has been embodied within one production step, so that manufacturing-related deviations from target values, in particular with regard to the dimensions of second dielectric layer 20, particularly with regard to the layer thicknesses d1, d2 of second dielectric layer 20, are reflected similarly in measurement capacitor device 12 and in compensation capacitor device 22.

According to the first embodiment, segment 20' of second dielectric layer 20 covers that surface 24-S of third electrode 24 which faces away from oxide layer 27 in part, preferably at a proportion of more than 50%, in particular more than 90%. In addition, segment 20' of second dielectric layer 20 covers that surface 25-S of fifth electrode 25 which faces away from oxide layer 27 in part, preferably at a proportion of more than 50%, in particular more than 90%. A gap 51 that is embodied between third electrode 24, fifth electrode 25, and oxide layer 27 is also substantially filled up by segment 20' of the second dielectric layer. "Substantially" is intended to mean here that manufacturing-related deviations, for example small bubbles, can be encompassed.

A fourth electrode 26 is embodied at a surface 20-S of first segment 21-1 of second dielectric layer 20 which faces away from third and fifth electrode 24, 25, surface 20-S also facing away from substrate 50. Segment 20' of the second dielectric layer is thus embodied between third electrode 24 and fourth electrode 26, which can be regarded as capacitor plates. For manufacturing reasons, segment 20' of the second dielectric layer is likewise embodied with the second layer thickness d2, as is that segment of second dielectric layer 20 which is disposed in the measurement capacitor device. A ratio between the first layer thickness d1 and the second layer thickness d2 can be known thanks to the known production step for manufacturing the second dielectric layer, and can be, for example, 5:3.

Compensation capacitor device 22 thus has a second electrical capacitance C2 that is traceable in part to third and fourth electrode 24, 26 in conjunction with second dielectric layer 20. Third electrode 24 is electrically contactable via a third electrical contacting device 19-3, for example a bonding pad. Fifth electrode 25 is electrically contactable via a fourth electrical contacting device 19-4, for example a bonding pad. A third electrical capacitance, which is traceable to third and fourth electrode 24, 26 in conjunction with second dielectric layer 20 and to fourth and fifth electrode 26, 25 in conjunction with second dielectric layer 20, is thus measurable between third and fourth electrical contacting device 19-3, 19-4. The second electrical capacitance C2 and the third electrical capacitance are substantially independent of atmospheric humidity, while the first electrical capacitance C1 is dependent on the atmospheric humidity that is to be measured.

Referring again to FIG. 1, measurement capacitor device 12 and compensation capacitor device 22 are connected in parallel or connectable in parallel by way of a circuit device 46 that is disposed on substrate 50.

Figure 5:
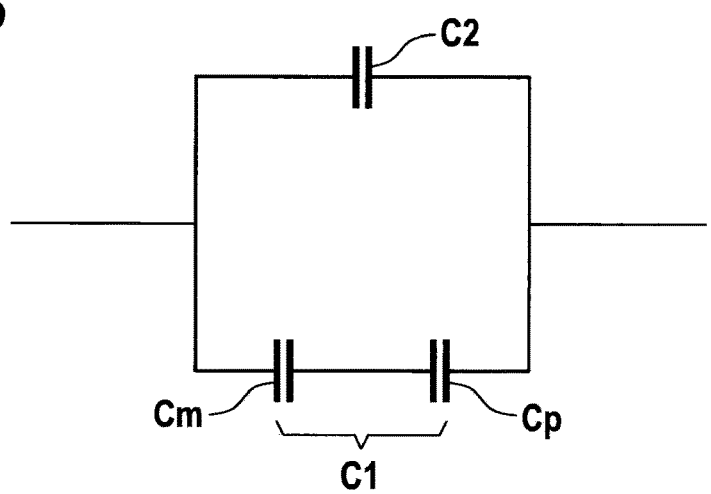
FIG. 5 is an equivalent diagram for the measurement capacitor device and the compensation capacitor device of the apparatus according to the first embodiment of the present invention, in a parallel circuit.

FIG. 5 is an equivalent circuit diagram for measurement capacitor device 12 and compensation capacitor device 22 of the apparatus according to the first embodiment, in a parallel circuit.

FIG. 1 further shows a measurement device 40 of apparatus 10, by way of which a first instantaneous capacitance value of a total electrical capacitance of the parallel electrical circuit of measurement capacitor device 12 with compensation capacitor device 22 is measurable. Measurement device 40 is electrically connected to circuit device 26. A measurement using measurement device 40 can be accomplished, for example, based on measurement of an RC time constant, of a phase shift, of a frequency modulation, and/or of an amplitude modulation. Measurement device 40 can encompass respectively corresponding electronic constituents.

According to the first embodiment, apparatus 10 furthermore has an identification device 42 with which, based on the measured first instantaneous capacitance value, a sensitivity of apparatus 10 with respect to atmospheric humidity is identifiable. Identification device 42 is electrically connected to measurement device 46 in order to receive at least the first instantaneous capacitance value measured by measurement device 40. Identification device 42 can be embodied, for example, as a computer of an equalization system. The identification of sensitivity can be carried out using one of the methods according to the present invention, as described in further detail below.

Apparatus 10 furthermore has a computation device 44 with which, based on the identified sensitivity of apparatus 10 and based on a measured third instantaneous capacitance value of the total electrical capacitance of the parallel circuit of measurement capacitor device 12 with compensation capacitor device 22, the value of the atmospheric humidity which is to be identified is identifiable. Computation device 44 has a nonvolatile data memory 45 for storing computation parameters. The identification of the atmospheric humidity value can be carried out according to one of the methods according to the present invention, as described in further detail below.

Apparatus 10 furthermore has an interface 48 with which results of the identification of the atmospheric humidity value can be outputted. The interface can be a wireless interface, e.g. a radio interface, or a simple wire-conducted interface, with which an analog or digital signal that encompasses the identified atmospheric humidity value is transmittable. The data input of data memory 45, for example a control program that is stored in data memory 45 and automatically controls identification by way of apparatus 10 of the value that is to be identified, can also be adaptable via interface 48.

Figure 6:
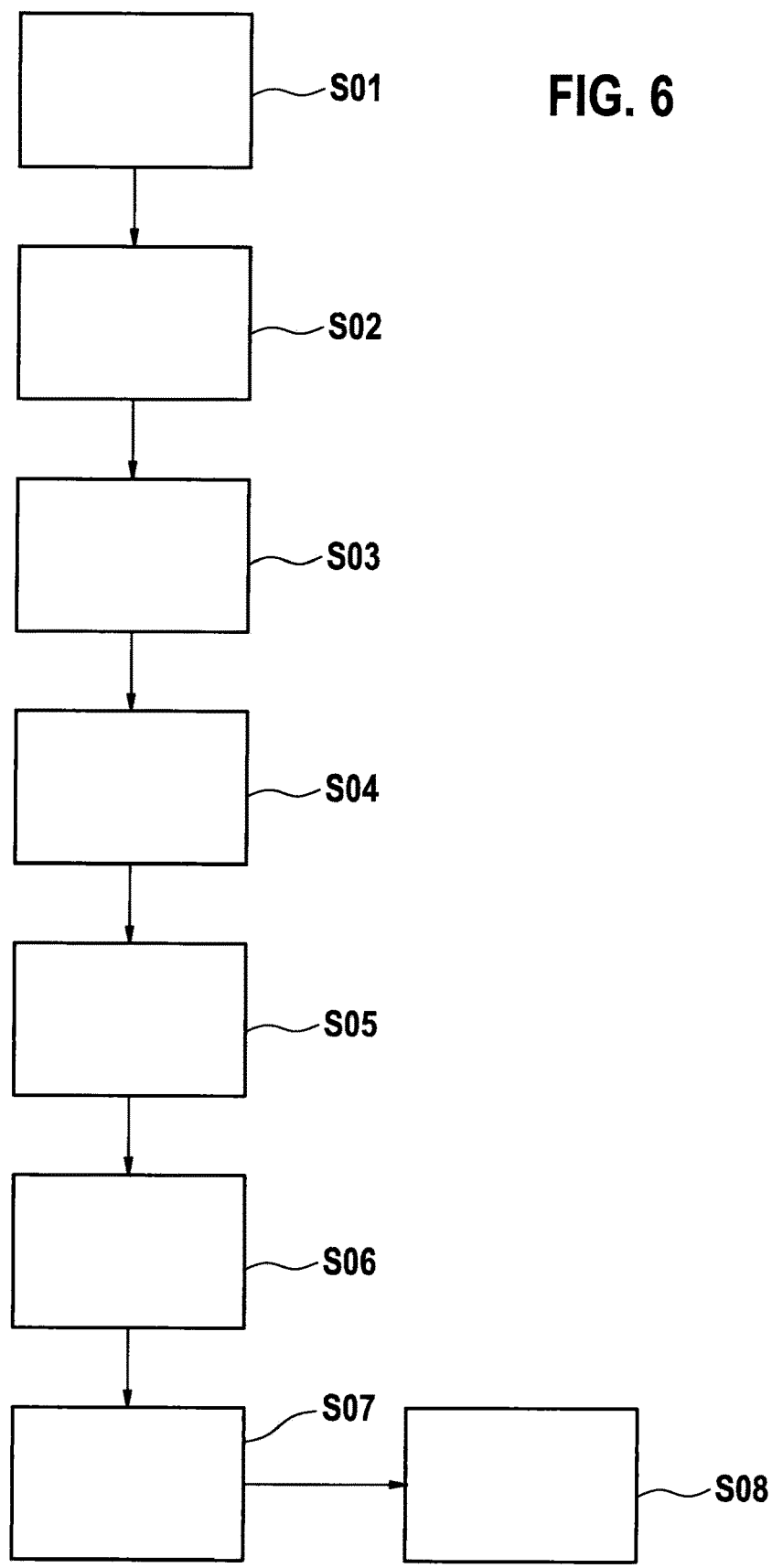
FIG. 6 is a schematic flow chart to explain a method for operating an apparatus for identifying a value of a property of a fluid which is to be measured, according to a second embodiment of the present invention.

FIG. 6 is a schematic flow chart to explain a method for operating an apparatus for identifying a value of a property of a fluid F which is to be measured, according to a second embodiment of the present invention, in particular a method for operating apparatus 10 for identifying an atmospheric humidity value according to the first embodiment of the present invention. The method according to the second embodiment is explained hereinafter principally with reference to apparatus 10 according to the first embodiment of the present invention. For the method according to the second embodiment, measurement capacitor device 12 and compensation capacitor device 22 should be connectable in parallel and also decouplable again from one another.

In a step S01, measurement capacitor device 12 is brought into contact with a reference fluid, the reference fluid having a predetermined reference value of the property that is to be identified. According to the second embodiment, the reference fluid is air having a predefined atmospheric humidity reference value, for example 50% atmospheric humidity. Alternatively, an atmospheric humidity of (within the context of technical capabilities) 0% or 100% can be used as an atmospheric humidity reference value. According to the second embodiment, the entire apparatus 10 is introduced for this purpose into a closed space that contains, as a reference fluid, air having a reference value of 10% atmospheric humidity.

In a step S02, while measurement capacitor device 12 is brought into contact with the reference fluid, a first instantaneous capacitance value of a total electrical capacitance of a parallel electrical circuit of measurement capacitor device 12 with compensation capacitor device 22 is measured. Measurement S02 can be accomplished, for example, based on measurement of an RC time constant, of a phase shift, of a frequency modulation, and/or of an amplitude modulation.

In a step S03, the sensitivity of apparatus 10 with respect to atmospheric humidity is identified based on the measured first instantaneous capacitance value and on the predetermined first reference value of the property of the reference fluid which is to be measured.

Predetermined parameters are taken into account in the identification of the sensitivity of apparatus 10. A predetermined parameter can, for example, indicate the average sensitivity exhibited by a plurality of apparatuses, which have been manufactured in the same manner as the present apparatus 10, as a function of the respective measured first instantaneous capacitance value, i.e. in a context of contact with the reference fluid.

Further predetermined parameters that are used for identifying the sensitivity are known properties of the polyimide from which first dielectric layer 18, embodied as a polyimide layer, is embodied, in particular a function that indicates as a function of atmospheric humidity the dielectric constant of the polyimide being used.

Further predetermined parameters that are used for identifying the sensitivity are known dimensions, in particular target values of the dimensions, of measurement capacitor device 12 and of compensation capacitor device 22.

A further predetermined parameter that is used for identifying the sensitivity is the reference value of the reference fluid.

In a step S04, a fourth instantaneous capacitance value of the first electrical capacitance of measurement capacitor device 12 in a context of contact between measurement capacitor device 12 and the reference fluid is measured, for example using measurement device 40 of apparatus 10 according to the first embodiment. The designation as "fourth instantaneous capacitance value" was selected because a "second instantaneous capacitance value" and a "third instantaneous capacitance value" are also defined elsewhere. The reference fluid exhibits the predetermined reference value of the property that is to be measured, i.e. is air having an atmospheric humidity of 10%. For step S04, the parallel connection between measurement capacitor device 12 and compensation capacitor device 22 has been nullified, for example by way of circuit device 46 according to the first embodiment. Measuring S04 can be accomplished, for example, based on a measurement of an RC time constant, of a phase shift, of a frequency modulation, and/or of an amplitude modulation.

In a step S05, a difference value between the measured first and measured fourth instantaneous capacitance value is identified. The difference value provides an indication as to how much influence compensation capacitor device 22 has on the total electrical capacitance. The difference value is, for example, calculated using computation device 44 of apparatus according to the first embodiment, and is stored in nonvolatile data memory 45 of computation device 44.

Calibration of the individual apparatus can therewith be completed. Steps S01 to S05 can be carried out, for example, once for each individual apparatus, which can then be used for one-time or repeated identification of the value that is to be identified of the property of fluid F which is to measured, with no need for further calibration. The further steps S06 to S08 can thus be carried out arbitrarily often, in particular later in time than steps S01 to S05.

In a step S06, measurement capacitor device 12 is brought into contact with fluid F having the property that is to be measured.

In a step S07, a second instantaneous capacitance value of measurement capacitor device 12, in a context of contact between measurement capacitor device 12 and fluid F having the property that is to be measured, is measured, for example using measurement device 40 of apparatus 10 according to the first embodiment. The measurement S07 can be accomplished, for example, based on a measurement of an RC time constant, of a phase shift, of a frequency modulation, and/or of an amplitude modulation.

Figure 9:
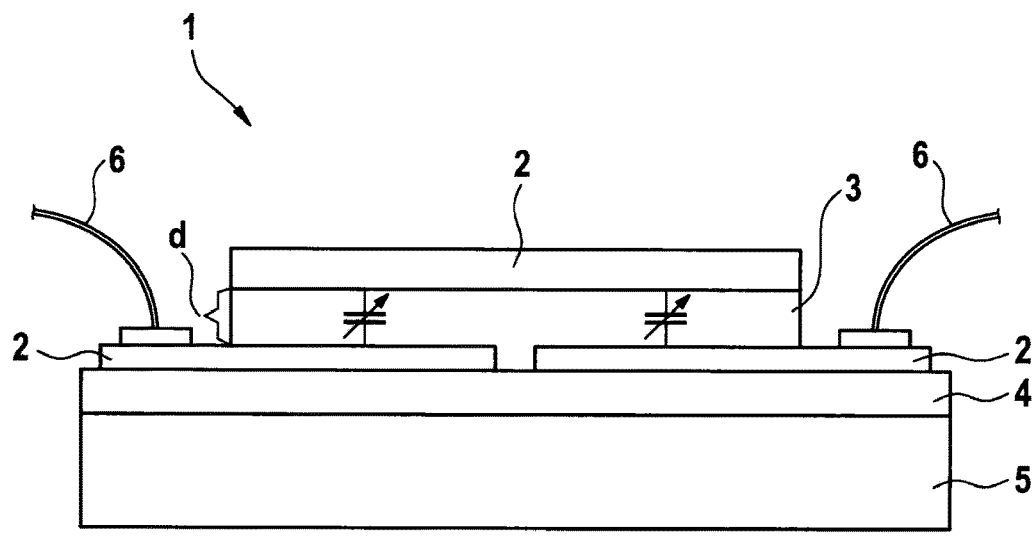
FIG. 9 is a schematic cross-sectional view through an exemplifying apparatus for capacitive measurement of an atmospheric humidity.

In a step S08, the value that is to be identified of the property of fluid F which is to be measured is identified based on the measured second instantaneous capacitance value, based on the identified sensitivity of the apparatus with respect to the property that is to be measured, and based on the ascertained difference value between the measured first and measured fourth instantaneous capacitance value. In particular, the difference value can be added to the measured second instantaneous capacitance value in order to obtain an effective capacitance value on which (rather than directly on the measured second instantaneous capacitance value) further identification of the value is based. The reference value can furthermore also be used, for example as an offset as described above with reference to FIG. 9, in the identification of the value that is to be identified.

Figure 7:
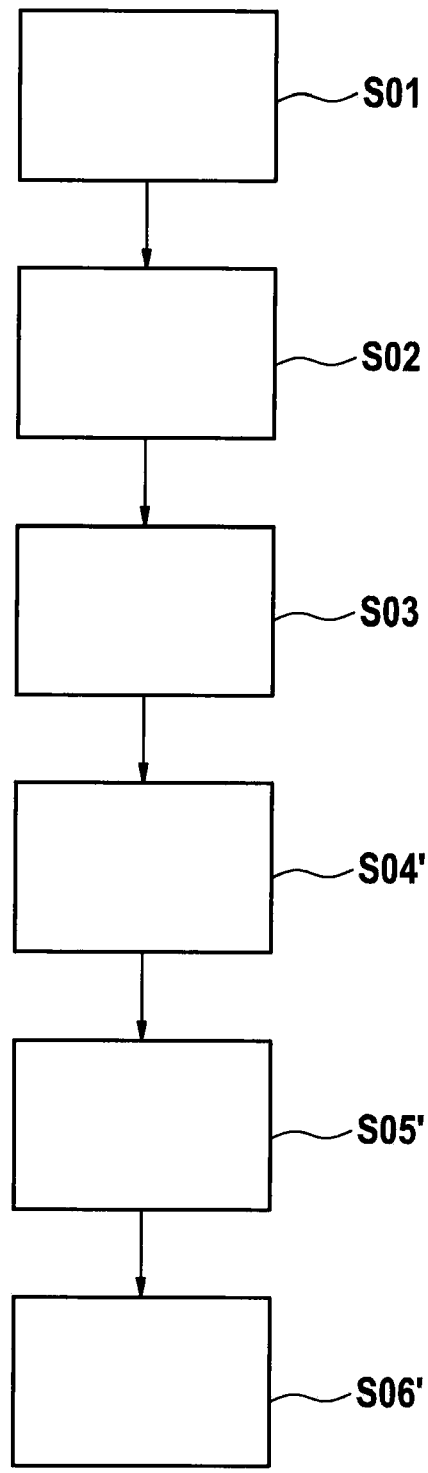
FIG. 7 is a schematic flow chart to explain a method for operating an apparatus for identifying a value of a property of a fluid which is to be measured, according to a third embodiment of the present invention.

FIG. 7 is a schematic flow chart to explain a method for operating an apparatus for identifying a value of a property of a fluid F which is to be measured, according to a third embodiment of the present invention, in particular a method for operating apparatus 10 for identifying an atmospheric humidity value according the first embodiment of the present invention. The method according to the third embodiment is also described principally with reference to apparatus 10 according to the first embodiment, which can be embodied to carry out both the method according to the second embodiment and the method according to the third embodiment.

The method according to the third embodiment is a variant of the method according to the second embodiment, which shares with it steps S01 to S03. For the method according to the third embodiment, measurement capacitor device 12 and compensation capacitor device 22 can be connectable in parallel as well as decouplable again from one another, measurements being carried out only when measurement capacitor device 12 and compensation capacitor device 22 are connected in parallel. Alternatively, measurement capacitor device 12 and compensation capacitor device 22 can also be permanently connected in parallel for the method according to the third embodiment.

In the method according to the third embodiment, calibration of the individual apparatus can be completed with steps S01 to S03. Steps S01 to S03 can be carried out, for example, once for each individual apparatus, which can then be used for one-time or repeated identification of the value that is to be identified of the property of fluid F which is to measured, with no need for further calibration. The further steps S04' to S06' can thus be carried out as often as desired, in particular later in time than steps S01 to S03.

According to the second embodiment, in a step S04' measurement capacitor device 12 is brought into contact with fluid F having the property that is to be measured.

In a step S05' a third instantaneous capacitance value of the total electrical capacitance of the parallel circuit of measurement capacitor device 12 with compensation capacitor circuit 22 in a context of contact between measurement capacitor device 12 and fluid F is measured, for example using measurement device 40 of apparatus 10 according to the first embodiment.

In a step S06' the value that is to be identified of the property of fluid F which is to be measured is identified based on the measured third instantaneous capacitance value and furthermore based on the identified sensitivity of the apparatus with respect to the property that is to be measured. What is identified here is the product of the sensitivity and the difference between the measured third instantaneous capacitance value and the measured first instantaneous capacitance value. The identified product can be added to a predetermined offset, for example to the reference value, in order to obtain as a result the value that is to be identified. The reference value can, for this purpose, be stored in data memory 45 of computation device 44.

Figure 8:
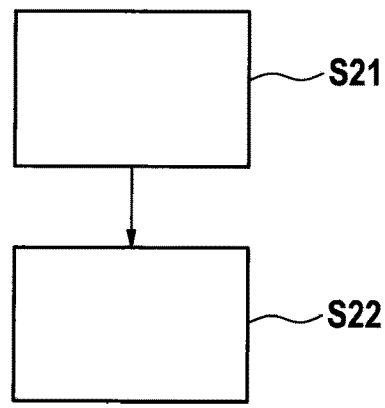
FIG. 8 is a schematic flow chart to explain a manufacturing method for an apparatus for identifying a value of a property of a fluid which is to be measured, according to a fourth embodiment of the present invention.

FIG. 8 is a schematic flow chart to explain a manufacturing method for an apparatus for identifying a value of a property of a fluid F which is to be identified, according to a fourth embodiment of the present invention, in particular a manufacturing method for apparatus 10 according to the first embodiment of the present invention. In particular with regard to the manufacturing method described, the reference characters of the steps are not intended to imply any chronological sequence. In particular, the individual steps can also be carried out in part simultaneously.

In a step S21 a measurement capacitor device 12 that is bringable into contact with fluid F is embodied in particular on a substrate 50.

The embodying S21 of measurement capacitor device 12 is accomplished in such a way that measurement capacitor device 12 is embodied with a first electrode 14 and a second electrode 16 and with a first dielectric layer 18 and a second dielectric layer 20.

The embodying S21 is furthermore accomplished in such a way that a first dielectric constant of first dielectric layer 18 in a context of contact with fluid F is dependent on a property of fluid F which is to be measured; and that a second dielectric constant of second dielectric layer 20 is substantially independent of the property of fluid F which is to be measured.

The embodying S21 is furthermore accomplished in such a way that measurement capacitor device 12 exhibits a first electrical capacitance C1 that is traceable at least in part to first and second electrode 14, 16 in conjunction with first dielectric layer 18 and with second dielectric layer 20.

In a step S22 a compensation capacitor device 22, which has second dielectric layer 20, a third electrode 24, and a fourth electrode 26, is embodied.

Compensation capacitor device 22 is furthermore embodied in such a way that compensation capacitor device 22 exhibits a second electrical capacitance C2 that is traceable at least in part to third and fourth electrode 24, 26 in conjunction with second dielectric layer 20.

Advantageously, measurement capacitor device 12 and compensation capacitor device 22 are embodied in such a way that the second electrical capacitance C2 accounts for between 1% and 400% of the first electrical capacitance C1, preferably between 5% and 300%, in particular between 10% and 200%, particularly preferably between 20% and 50%.

According to the fourth embodiment, first dielectric layer 18 and second dielectric layer 20 are embodied between first electrode 14 and second electrode 16. Second dielectric layer 20 is furthermore embodied between third electrode 24 and fourth electrode 26.

In addition, second dielectric layer 20 is embodied in the same production step between first electrode 14 and second electrode 16 and between third electrode 24 and fourth electrode 26, so that second dielectric layer 20 both of measurement capacitor device 12 and of compensation capacitor device 22 exhibits the same manufacturing-related deviations from target values, in particular as regards the first and the second layer thickness d1, d2 of second dielectric layer 20.

Both the embodiment S21 of measurement capacitor device 12 and the embodiment S22 of compensation capacitor device 22 are accomplished advantageously at a wafer level. A plurality of apparatuses can thus be manufactured simultaneously with particularly little total technical outlay.

According to a fifth embodiment of the present invention, both the measurement capacitor device and the compensation capacitor device are embodied as interdigital capacitors. The fifth embodiment is a variant of the first embodiment, compensation capacitor device 22 according to the first embodiment being replaced by a compensation capacitor device embodied as an interdigital capacitor.

The compensation capacitor device according to the fifth embodiment, embodied as an interdigital capacitor, is embodied as a variant of measurement capacitor device 12 according to the first embodiment shown in FIGS. 2 and 3, an electrically conductive layer of an electrically conductive material, for example of a metal, being embodied instead of first dielectric layer 18. It is preferred here that the conductive material exhibit substantially no sensitivity with respect to the property of the fluid which is to be measured, i.e. exhibit a dielectric constant independent of the property that is to be measured.

The dimensions, in particular layer thicknesses, in the case of the compensation capacitor device according to the fifth embodiment, embodied as an interdigital capacitor, can likewise be embodied differently than in the case of measurement capacitor device 12 according to the first embodiment. It can be advantageous in particular if a gap width between the electrode fingers of the compensation capacitor device is 0.5 to 2 times the size of the gap width (d4 in FIG. 3) between the electrode fingers of the measurement capacitor device, in particular 0.75 to 1.5 times the size, particularly preferably the same size.

Second dielectric layer 20 is embodied in the same production step, from the same material, and in the same manner (e.g. by vacuum deposition) in the context of the measurement capacitor devices and compensation capacitor devices embodied as interdigital capacitors. The properties of second dielectric layer 20 thus behave substantially similarly in the measurement capacitor device and in the compensation capacitor device. In particular, material parameters as well as geometric parameters—which vary for manufacturing reasons and are to be identified for the capacitance—of second dielectric layer 20 behave substantially similarly. This is very particularly true for the first and the second layer thickness d1, d2 of second dielectric layer 20, which are thus, independently of the possibly different dimensions of the electrode fingers, the same for the measurement capacitor device and the compensation capacitor device according to the fifth embodiment.

Although the present invention has been described above with reference to preferred exemplifying embodiments, it is not limited thereto but is instead modifiable in numerous ways. In particular, the invention can be changed or modified in a multiplicity of ways without deviating from the essence of the invention. For example, further protective layers, but also layers having or made of plastic, having or made of epoxy, etc., can be disposed between substrate 50 and first to fifth electrodes 14, 16, 24, 25, 26.

For example, both the measurement capacitor device and the compensation capacitor device can be embodied as interdigital capacitors, or also both as plate capacitors, or also as capacitors of a different design. Manufacture can be particularly simple if the measurement capacitor device and the compensation capacitor device are embodied as capacitors of the same design although possibly having different dimensions, for example of the electrodes and/or electrode fingers.

What is claimed is:

1. An apparatus for identifying a value of a property of a fluid which is to be measured, comprising:
    a measurement capacitor device which is contactable with the fluid, including:
        a first electrode,
        a second electrode,
        a first dielectric layer,
        a second dielectric layer, the first electrode, the second electrode, the first dielectric layer, and the second dielectric layer being disposed so that a first electrical capacitance of the measurement capacitor device is traceable at least in part to the first electrode and the second electrode in conjunction with the first dielectric layer and with the second dielectric layer,
        a first dielectric constant of the first dielectric layer being dependent, in a context of contact with the fluid, on the property of the fluid which is to be measured,
        a second dielectric constant of the second dielectric layer being substantially independent of the property of the fluid which is to be measured;
    a compensation capacitor device that has the second dielectric layer, a third electrode, and a fourth electrode, the second dielectric layer, the third electrode, and the fourth electrode being disposed so that a second electrical capacitance of the compensation capacitor device is traceable at least in part to the third and the fourth electrodes in conjunction with the second dielectric layer, and the compensation capacitor device being connected in parallel, or connectable in parallel, with the measurement capacitor device;
    a measurement device to measure a first instantaneous capacitance value of a total electrical capacitance of a parallel electrical circuit of the measurement capacitor device with the compensation capacitor device;
    an identification device to determine, based on the measured first instantaneous capacitance value, a sensitivity of the apparatus with respect to the property that is to be measured; and
    a computation device to determine the value that is to be identified of the property of the fluid which is to be measured.

2. The apparatus as recited in claim 1, wherein at least one of:

the first dielectric layer and the second dielectric layer are embodied between the first electrode and the second electrode, and the second dielectric layer is embodied between the third electrode and the fourth electrode.

3. The apparatus as recited in claim 1, wherein the computation device determines the value based on the identified sensitivity of the apparatus and based on at least one of: (i) a measured second instantaneous capacitance value of the first electrical capacitance of the measurement capacitor device, and (ii) a measured third instantaneous capacitance value of the total electrical capacitance of the parallel circuit of the measurement capacitor device with the compensation capacitor device.

4. The apparatus as recited in claim 1, wherein the first dielectric layer includes a polyimide.

5. The apparatus as recited in claim 1, wherein at least one of the measurement capacitor device and the compensation capacitor device includes one of a plate capacitor and an interdigital capacitor.

6. The apparatus as recited in claim 1, wherein:

the fluid is a one of gas and a gas mixture, and the property of the one of the gas and the gas mixture which is to be identified is a concentration of a predetermined substance in the one of the gas and the gas mixture, the first dielectric constant of the first dielectric layer changing substantially as a function of the concentration of water vapor in the gas or gas mixture.

7. The apparatus as recited in claim 1, wherein the fluid is a liquid, and wherein the property of the liquid which is to be identified is a pH of the liquid.

8. The apparatus as recited in claim 1, further comprising:

a controllable circuit device with which the compensation capacitor device is at least one of electrically connectable in parallel with the measurement capacitor device and electrically decouplable from the measurement capacitor device, wherein at least the measurement capacitor device and the compensation capacitor device are embodied on a substrate;

wherein the controllable circuit device is embodied as an application-specific integrated circuit.

9. The apparatus as recited in claim 6, wherein the concentration is a concentration of water vapor in the one of the gas and the gas mixture.

* * * * *